United States Patent [19]
Inoue

[11] Patent Number: 5,171,259
[45] Date of Patent: Dec. 15, 1992

[54] DEVICE FOR NONOPERATIVELY OCCLUDING A DEFECT

[76] Inventor: Kanji Inoue, 98-13, Miyazaki-cho Simogamo, Sakyo-ku, Kyoto-shi, Kyoto 606, Japan

[21] Appl. No.: 777,258
[22] PCT Filed: Mar. 30, 1991
[86] PCT No.: PCT/JP91/00426
§ 371 Date: Dec. 2, 1991
§ 102(e) Date: Dec. 2, 1991
[87] PCT Pub. No.: WO91/15155
PCT Pub. Date: Oct. 17, 1991

[30] Foreign Application Priority Data
Apr. 2, 1990 [JP] Japan ................................. 2-87774
Apr. 2, 1990 [JP] Japan ................................. 2-87775

[51] Int. Cl.⁵ ........................................... A61B 17/00
[52] U.S. Cl. .................................. 606/213; 606/232
[58] Field of Search .................. 606/213, 215, 232

[56] References Cited
U.S. PATENT DOCUMENTS

| 3,874,388 | 4/1975 | King et al. | 606/213 |
| 4,007,743 | 2/1977 | Blake | 606/213 |
| 4,917,089 | 4/1990 | Sideris | 606/215 |

FOREIGN PATENT DOCUMENTS
57-24132 5/1982 Japan.
58-27935 6/1983 Japan.

Primary Examiner—Stephen C. Pellegrino
Assistant Examiner—Gary Jackson
Attorney, Agent, or Firm—Wegner, Cantor, Mueller & Player

[57] ABSTRACT

The device of the invention is provided with a pair of patches each comprising a resilient, foldable annular frame and a piece of cloth stretched over and fixed to the frame. The patches are so arranged as to face each other across a gap and sewed together concentrically with a thread slightly inwardly of the outer circumferential edge thereof in such a manner that as the thread is pulled, the two patches are moved so as to approach each other.

4 Claims, 17 Drawing Sheets

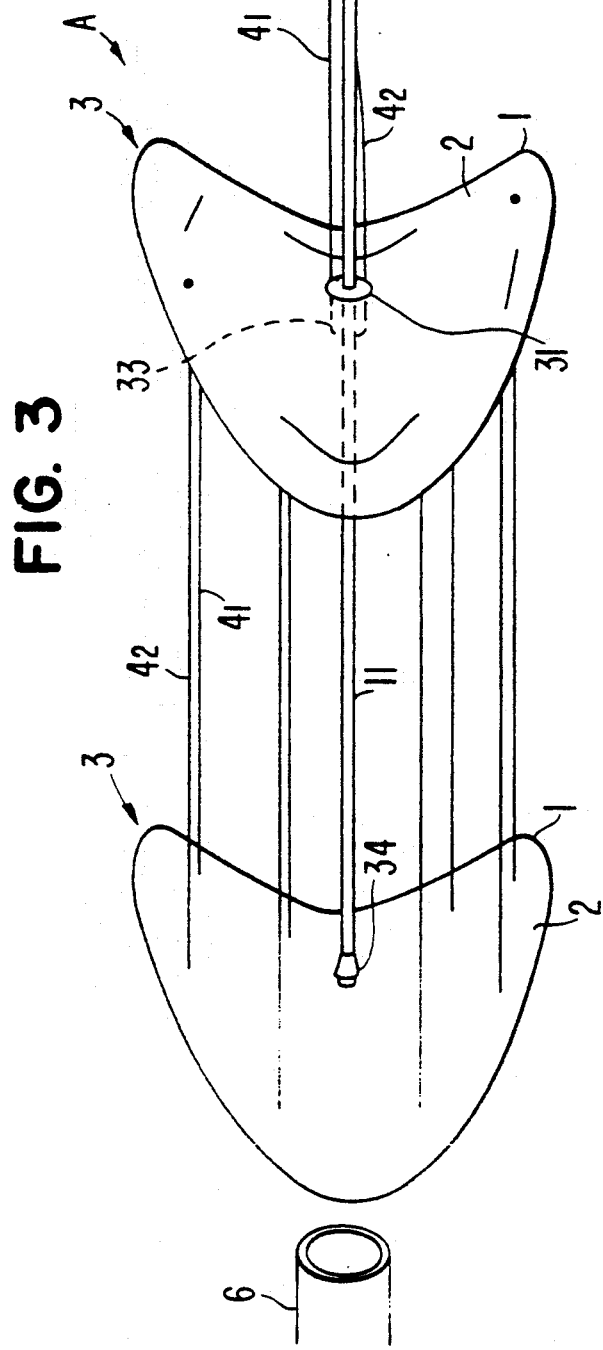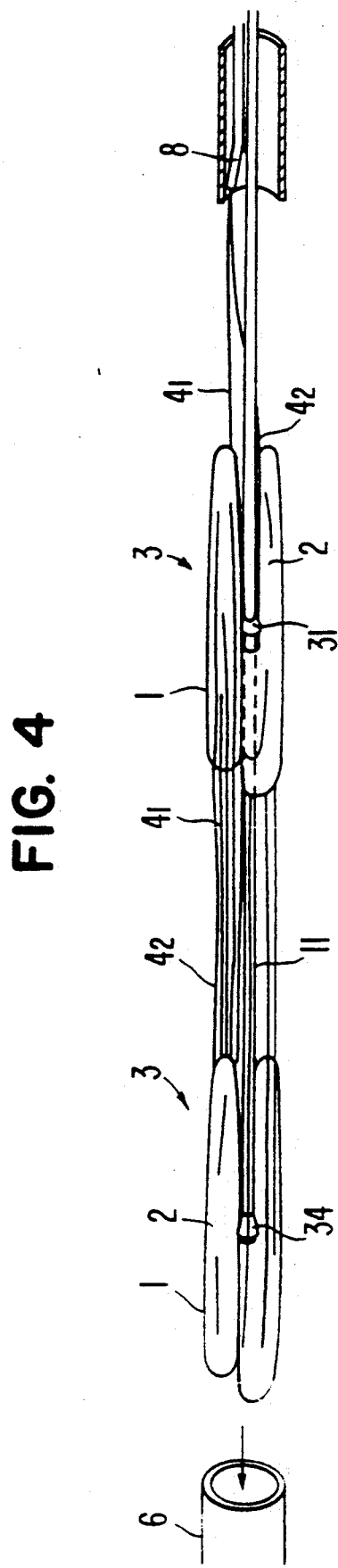

DEVICE FOR NONOPERATIVELY OCCLUDING A DEFECT

FIELD OF THE ART

This invention relates to a device for occluding a defect in in the heart such as septal defects nonoperatively, that is, without performing an open chest or other major surgical operation.

PRIOR ART

In some heart diseases such as septal defects a hole exits in the wall of the heart and blood is shunted through the hole. To treat the desease it has been customary to occlude the hole by a patch by performing an open chest operation.

A nonoperative method called the umbrella method has been developed in the United States.

The open chest method of treatment has a disadvantage that it involves a great lesion and leaves a scar in the surface of the patient's body.

According to the umbrella method, since a pair of patches are connected only at the central portions thereof, the defect to be occluded is not always positioned at the central portions of the patches, so that the patches may be displaced to cause leakage to occur or get out of the defect.

The invention has been accomplished in view of the above problems in the prior art. The object of the invention is to provide a device which can nonoperatively occlude a defect simply and certainly without leaving a scar in the surface of the body.

DISCLOSURE OF THE INVENTION

The device for nonoperatively occluding a defect according to the invention (which will be referred to as the occlusive device) is characterized by that a pair of patches, each of which comprises a resilient, foldable annular frame and a piece of cloth stretched over and fixed to the frame, are disposed opposite to each other with a gap therebetween and connected by a thread, which is led out of one of the patches in such a manner that by pulling the thread led out of the patch the two patches are caused to approach each other.

It is preferable to have the two patches sewed by a thread along a coaxial circle on each of the patches slightly inwardly of the circumferential edge thereof.

The thread is led out of one of the patches preferably at the center thereof.

Shrink-preventing members may be provided on that surface of one of the patches which faces the other so as to extend from a position slightly inward of the circumferential edge of the patch to a position near the center thereof.

The occlusive device of the above construction can be implanted in a defect in the following manner. The two patches, each of which comprises a resilient, foldable annular frame and a piece of cloth stretched over and fixed to the frame, are folded and inserted into a catheter and brought to the defect which is the objective position. Then, only the front patch beyond the defect is restored to its annular shape by the resiliency of the annular frame. Then, the rear patch in front of the defect is restored to its annular shape by the resiliency of the annular frame. Then, the thread extending from the rear patch is pulled so as to cause the two patches at the opposite sides of the defect to approach each other and hold the periphery of the defect therebetween. As a result, the defect can be nonoperatively occluded by the two patches simply and certainly without scarring the surface of the body.

If the two patches are sewed by a thread along a circle a little inward of the circumferential edge of each of the patches, the two patches are put together a little inward of the circumferential edge of the defect, so that the peripheral portions of the patches can hold the peripheral portion of the defect the more securely. With the thread led out of the patch at its central part, by pulling the thread it is possible to cause the two patches to approach each other efficiently in well-balanced condition.

With the shrink-preventing members provided on one of the patches in such a manner that they extend from a position a little inward of the periphery of the patch to a position near the center thereof, it is possible to prevent the patch from being shrunk in the radial direction when the thread is pulled, and occlude the defect by the two patches without fail.

BRIEF DESCRIPTION OF THE DRAWINGS

FIGS. 3 and 4 are perspective views showing the process of folding the occlusive device and inserting it into a catheter;

FIGS. 29 through 37 are views schematically showing the structures for connecting the central portions of the patches.

BEST MODES FOR EMBODYING THE INVENTION

Figure 1:
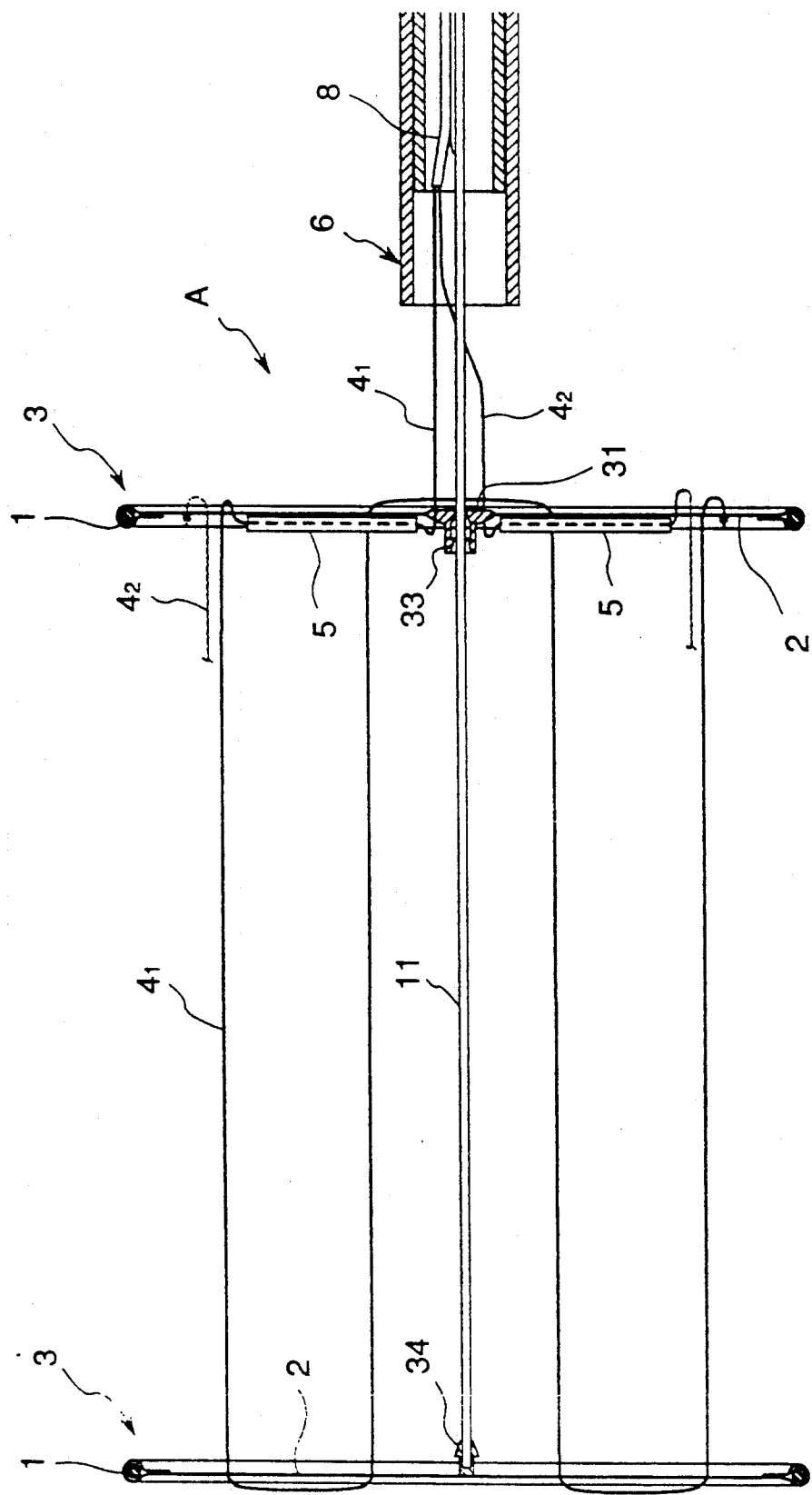
FIG. 1 is a side sectional view showing an occlusive device according to one embodiment of the invention.
Figure 2:
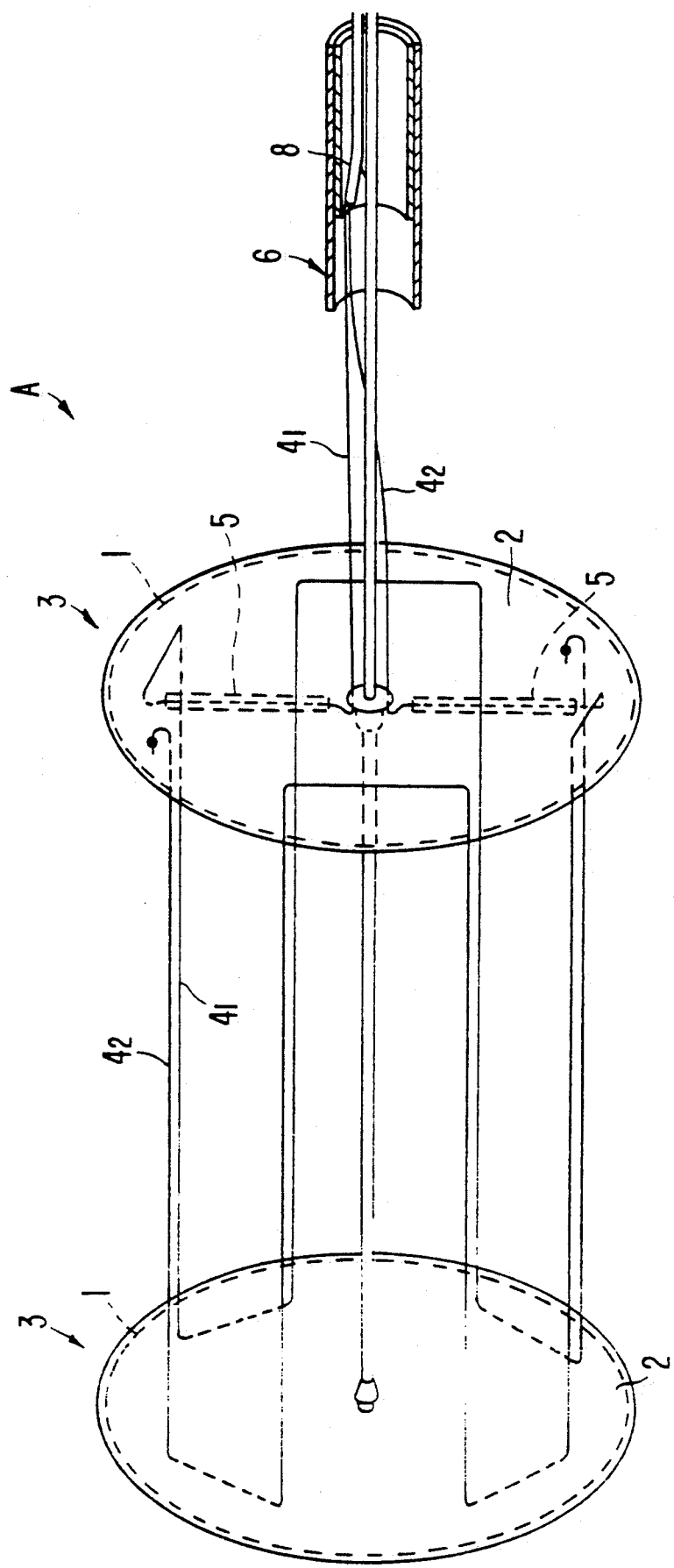
FIG. 2 is a perspective view of the occlusive device.

The invention will be described below in detail with reference to the embodiments thereof shown in the accompanying drawings.

The occlusive device A according to the invention comprises a pair of patches 3 and a thread 4. Each of the patches 3 comprises a resilient, foldable annular frame 1 and a piece of cloth 2 stretched over and fixed to the frame. The cloth 2 is sewed or otherwise fixed to the frame 1. The shape of the patches is not limited to a circle but may be an ellipse. The cloth 2 is made of polyester. It is not limitd to this material. The annular frame 1 is made of a flexible material highly capable of resilient restoration, such as a wire of Ti-Ni alloy. The material is not limited to the alloy. The two patches 3 are so arranged as to face each other across a gap and connected by a thread 4, one end portion of which extends outwardly of one of the patches 3 so that as the end portion of the thread 4 is pulled, the two patches 3 approach each other.

In the embodiment shown in FIGS. 1 through 17, the two patches 3 are alternatively sewed with a first thread $4_1$ making stitches along one half of a circle on each of the patches 3 radially inward of the circumferential edge thereof and with a second thread $4_2$ making stitches along the other half of the circle. Each of the threads $4_1$ and $4_2$ has its one end fixed to one of the patches 3 and the opposite end portion passing slidably through a reinforcing member 31 provided at the center of the patch 3, with a considerable length of the thread extending outwardly of the member 31. The reinforcing member 31 is made of rubber or the like, with the threads $4_1$ and $4_2$ being held by the reinforcing member 31 by friction. The reinforcing member 31 is provided at its center with a through hole 32, through which a carrying wire 11 slidably passes. An outer tube 33 projects from one end surface of the reinforcing member 31 and has an open end toward the opposite patch 3, at the center of which an inner tube 34 is fixed so as to be able to be inserted into the outer tube 33. Undercuts 33a and 34a engageable with each other are formed on the inner circumferential surface of the outer tube 33 and the outer circumferential surface of the inner tube 34, respectively. In this embodiment, the outer tube 33 is integral with the reinforcing member 31. Preferably, at least one of the outer and inner tubes 33 and 34 is made of plastic material such as synthetic resin.

In this embodiment, on the patch 3 from which the threads $4_1$ and $4_2$ are led out there are provided a pair of shrink-preventing members 35 for preventing deformation of the patches 3 when they are put together. The shrink-preventing members 5 are tubular members made of a material relatively low in resiliency, through which those portions of the threads $4_1$ and $4_2$ extending from the peripheral portion of the patch toward the reinforcing member 31 at the center thereof pass. Even when the end portions of the threads $4_1$ and $4_2$ which are led out of the patch are strongly pulled to tension the threads, the shrink-preventing members 5 effectively and certainly prevent the patch 3 from being deformed and shrunk so much that the patch 3 slips off the defect 7.

The occlusive device A of the above construction is introduced into a body by means of a catheter 6, and the carrying wire 11 and a thread cutter 8 inserted into the catheter. The carrying wire 11 is a metal wire hard to be bent. When the occlusive device A is to be inserted into a body, the forward end of the wire is slid through the hole 32 in the reinforcing member 31 provided on the rear patch 3 and press-fitted into the inner tube 34 of the front patch 3, so that the two patches 3 are held by friction on the carrying wire 11 in an opposed relation.

Figure 16:
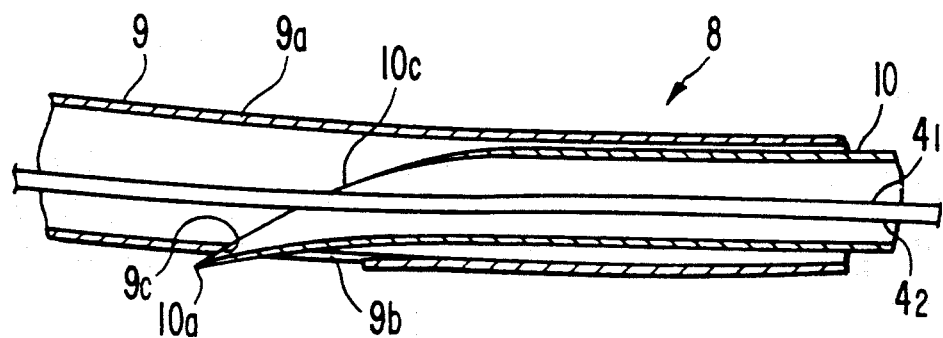
FIG. 16 is a sectional view showing a thread cutter used in the above embodiment.
Figure 17:
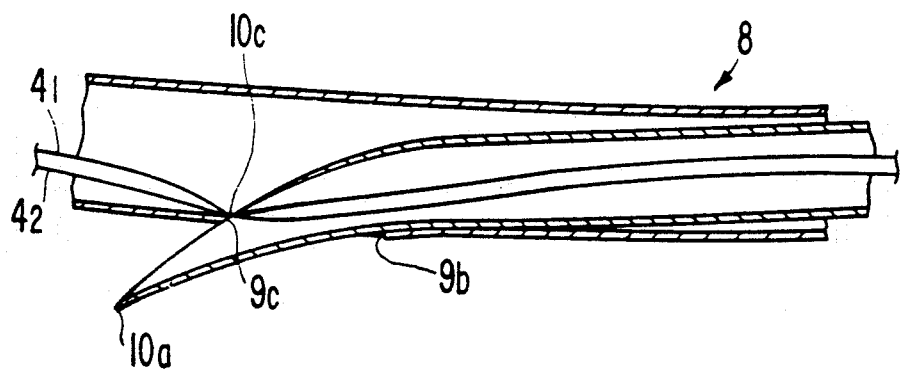
FIG. 17 is a view showing the operation of the thread cutter.

The thread cutter 8 is of a double tube construction comprising an outer metal tube 9 and an inner metal tube 10 slidably inserted into the outer tube 9, with the forward end portions thereof being shaped as shown in FIG. 16. In particular, the forward end portion 9a of the outer metal tube 9 is slightly curved and a lateral window 9b is formed in the curved portion 9a. The forward end portion of the inner metal tube 10 is cut aslant and the pointed end 10a thereof projects outside through the lateral window 9b of the outer metal tube 9. As the inner metal tube 10 is slid in such a direction that the pointed end 10a thereof projects farther outside, the cut edge 10c of the inner metal tube 10 comes into contact with the edge 9a of the above-mentioned lateral window 9b as shown in FIG. 17, so that the threads $4_1$ and $4_2$ introduced into the inner metal tube 10 from the forward end of the outer metal tube 9 are nipped and cut by the two edges 9c and 10c.

The steps of introducing the occlusive device A into a body by using the catheter 6, the wire 11 and the thread cutter 8 as mentioned above are as follows: First, the patch 3 positioned in front is folded in four and inserted into the catheter 6 through its rear end, and the other patch 3 positioned in the rear is folded in four and inserted into the catheter 6. FIG. 3 shows the patches 3 as they are being folded, and FIG. 4 shows the patches 3 completely folded to such a degree that they can be inserted into the catheter 6. The threads $4_1$ and $4_2$ connecting the two patches 3 extend outwardly from the patch 3 disposed in the rear. The threads $4_1$ and $4_2$ connecting the two patches 3 are kept slackened, and the end portions of the threads $4_1$ and $4_2$ leading from the rear patch 3 are passed through the outer and inner metal tubes 9 and 10 of the thread cutter 8 to lie outside so as to be able to be pulled outwardly.

The shrink-preventing members 5 need not be folded if the patch 3 with the members 5 is folded in such a manner that the members 5 lie in the same direction as the axis of the catheter 6. The thread cutter 8 and the carrying wire 11 are inserted into the catheter 6 through the rear end thereof, with the carrying wire 11 pushing the patches 3 forwardly in the catheter.

Figure 5:
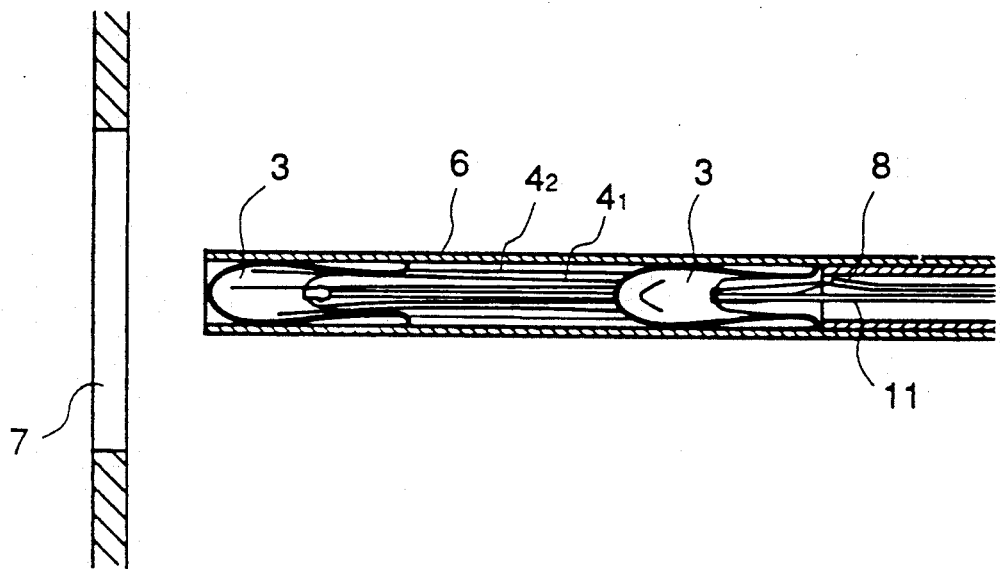
FIGS. 5, 6, 7, 8, 9, 10, 11 and 12 are side sectional views showing the process of implanting the occlusive device in a defect.
Figure 6:
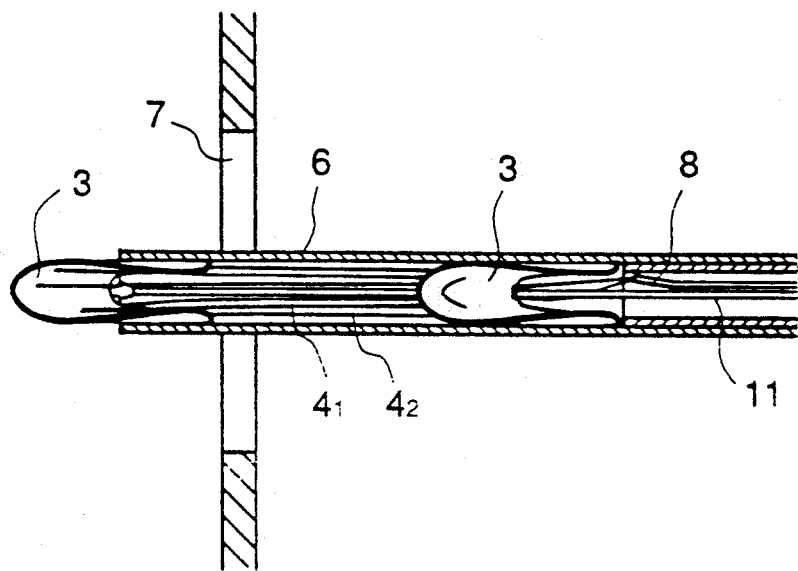
Figure 7:
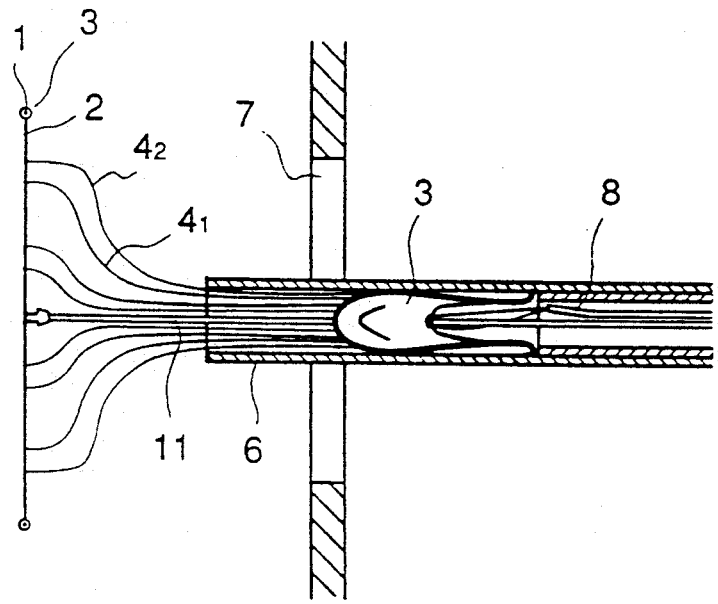
Figure 8:
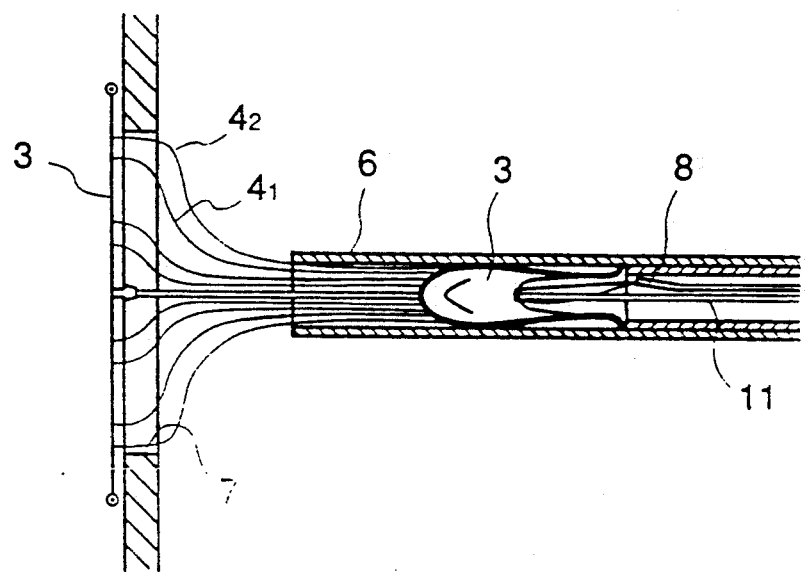
Figure 9:
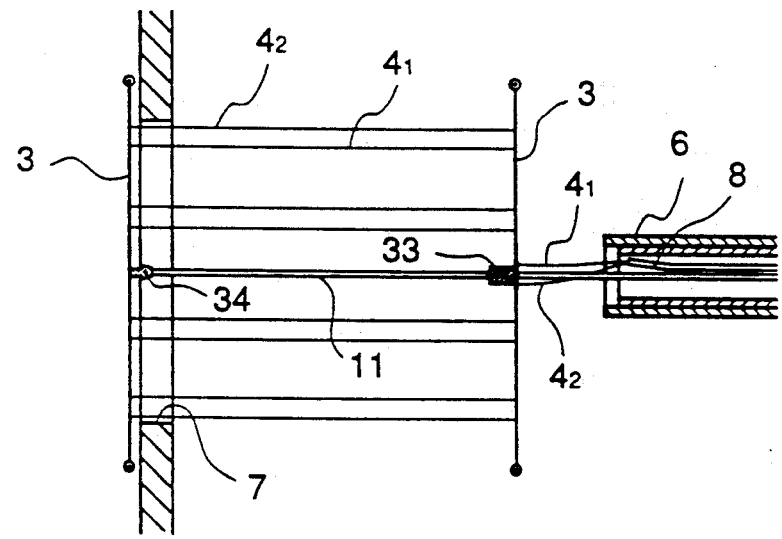
Figure 10:
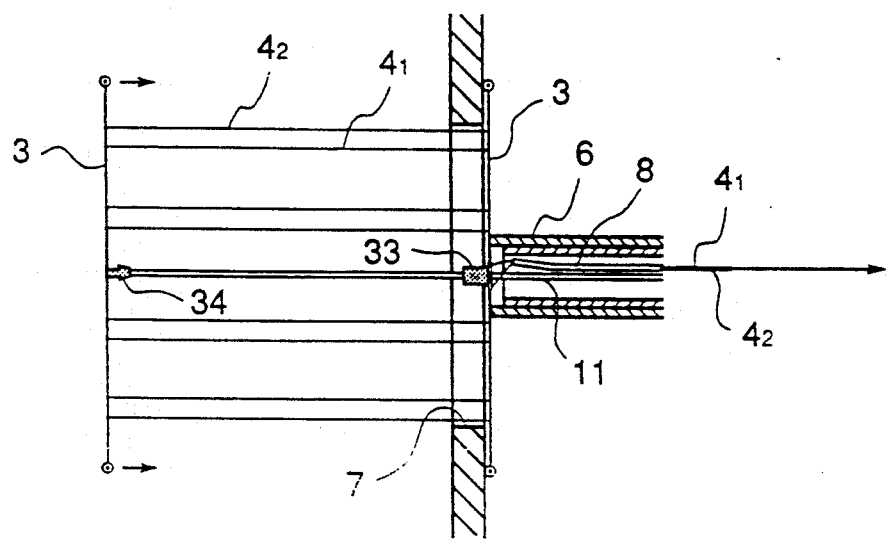

For actual operation within a body, the catheter 6 is inserted into the femoral vein near the groin as far as the front end of the catheter 6 comes near the defect 7 as shown in FIG. 5 and passes through the defect 7 as shown in FIG. 6. Then, the front patch 3 is pushed out of the catheter 6 to reside at the remote side of the defect 7 as shown in FIG. 7, whereupon the patch 3 automatically expands beyond the defect 7 due to the resiliency of the resilient, foldable annular frame 1. Then, the catheter 6 is drawn as far as the front end thereof comes back to the near side of the defect 7 as shown in FIG. 8. With the carrying wire 11 fixed at the position, the catheter 6 alone is farther drawn, so that the rear patch 3 is also released from within the catheter 6 as shown in FIG. 9. Then, the patches 3 at both sides are put together to occlude the defect 7 in the following manner. As shown in FIG. 10, with the front and rear patches 3 disposed at the remote and near sides, respectively, of the defect 7, the front end of the catheter 6 is applied to the outer surface of the rear patch 3 and the threads $4_1$ and $4_2$ are pulled, whereupon the front patch 3 is drawn rearwardly into contact with the rear patch 3, with the carrying wire 11 sliding rearwardly against a slight resistance provided by the reinforcing member 31 of the rear patch 3. Then, as the threads $4_1$ and $4_2$ are strongly pulled, the peripheral portions of the cloths 2 of the patches 3 sewed together with the treads are strongly drawn together thereby to hold the periphery of the defect 7 therebetween the more securely. The nearer the circle along which the patches are sewed is to the size of the defect 7, the more securely the patches occlude the defect 7 to prevent leakage therethrough. As the threads $4_1$ and $4_2$ are pulled strongly, the two patches 3 are put together strongly so as to hold therebetween the periphery of the defect 7 strongly.

Figure 11:
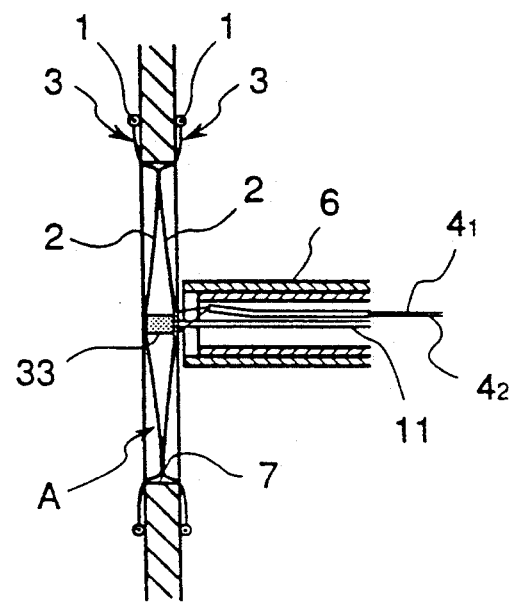
Figure 12:
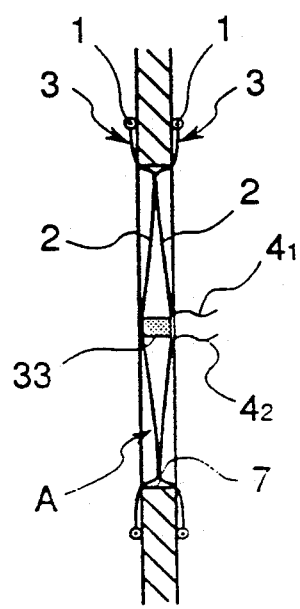

When the two patches 3 have been closely put together as shown in FIG. 11, the carrying wire 11 is pulled back strongly with the catheter 6 being held against the rear patch 3, whereupon the front end of the carrying wire 11 is pulled out of the resilient inner tube 34 on the front patch 3 into the catheter 6. Then, as the inner metal tube 10 of the thread cutter 8 is pushed forwardly into the outer metal tube 9 thereof, the threads $4_1$ and $4_2$ are cut in the manner previously mentioned, whereupon the occlusive device A has been separated from the catheter 6, the carrying wire 11 and the thread cutter 8 thereby to complete occlusion of the defect 7 as shown in FIG. 12.

Figure 13:
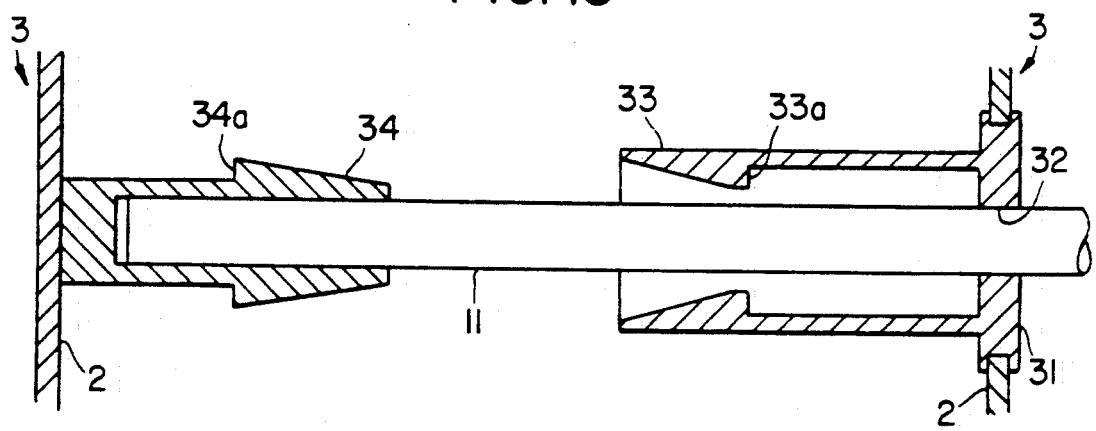
FIGS. 13, 14 and 15 are side sectional views showing in an enlarged scale the outer and inner tubes provided at the center of the occlusive device.
Figure 14:
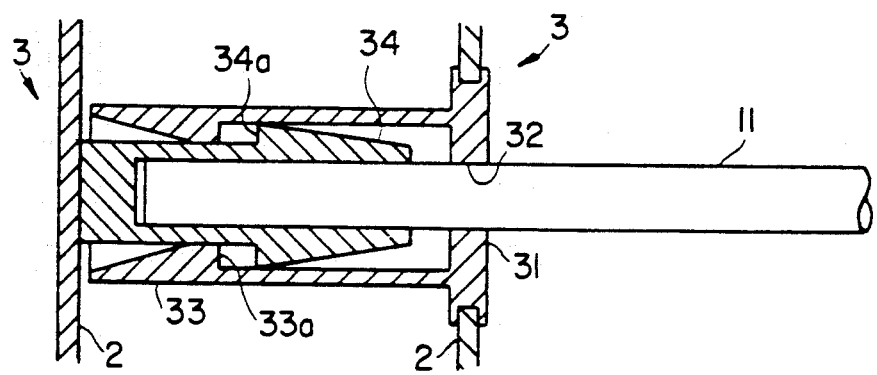
Figure 15:
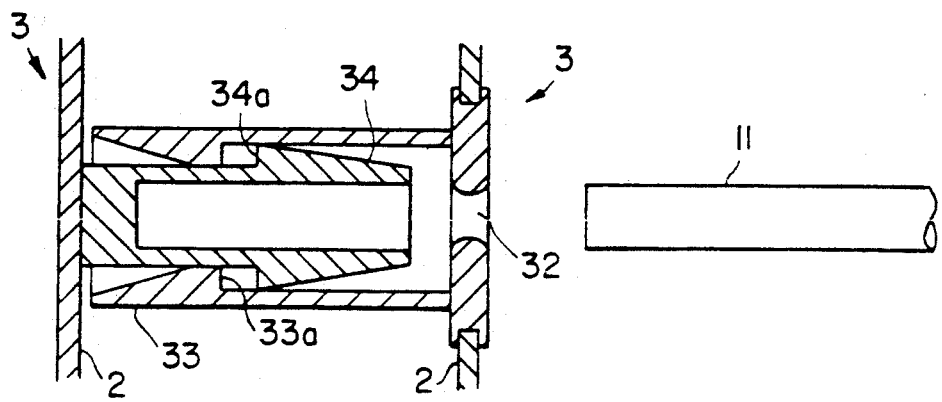

As the two patches 3 are put together at the sewed portions thereof, the inner tube 34 provided on the front patch 3 is fitted into the outer tube 33 provided on the rear patch 3 while being resiliently deformed, and the undercuts 34a and 33a formed on the inner and outer tubes 34 and 33 engage each other inseparably. FIG. 13 shows the inner tube 34 immediately before it is inserted into the outer tube 33; FIG. 14 shows the inner tube 34 having been fitted into the outer tube 33; and FIG. 15 shows the carrying wire 11 having been pulled out of the inner tube 34.

Figure 18:
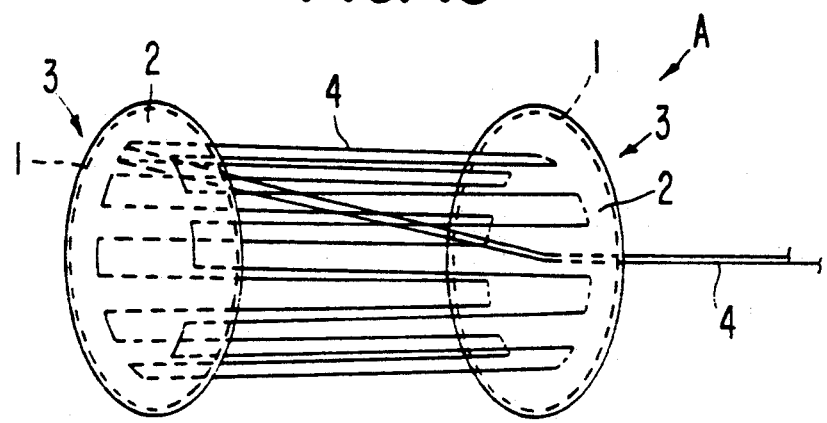
FIG. 18 is a perspective view of an occlusive device according to another embodiment of the invention.
Figure 22:
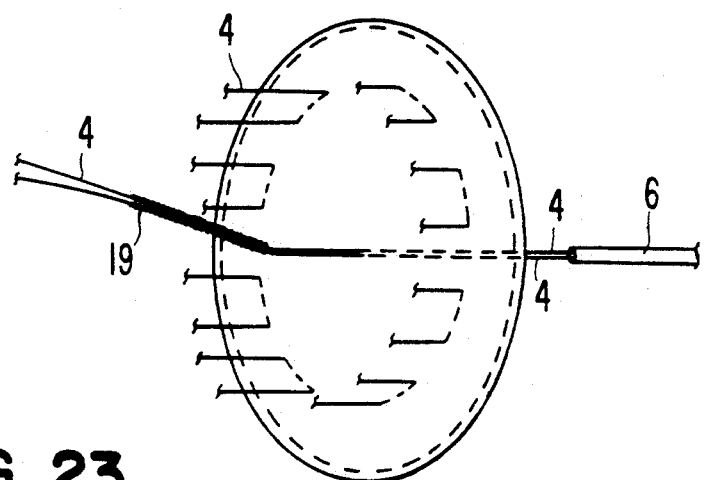
FIGS. 22 and 23 are perspective views showing different manners of leading the thread out of the patch.
Figure 23:
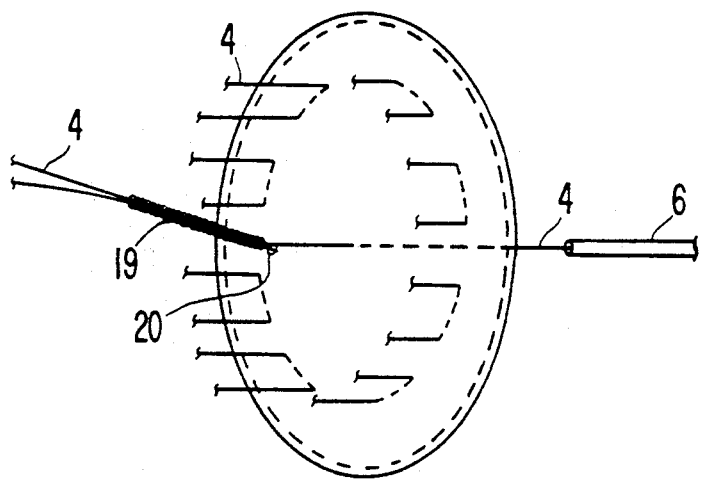

FIG. 18 shows another embodiment of the occlusive device A. In this embodiment, a pair of patches 3 are alternately sewed with a continuous length of thread 4 making stitches along a coaxial circle slightly inward of the peripheral edge of each of the patches 3. The opposite ends of the thread 4 are drawn out of the central portion of one of the patches 3 so as to extend a considerable length therefrom. As shown in FIG. 22, a different thread 19 may be coiled around and hold those portions of the thread 4 which lie adjacent the central portion of the patch 3 through which the thread passes. The thread 19 coiled around the portions of the thread 4 helps prevent the thread 4 from being slackened after the end portions of the thread 4 connecting the patches 3 have been pulled to put the patches 3 together. As shown in FIG. 23, a knot 20 may be formed at one end of the thread 4 so that it may not be separated from the coiled thread 19, with the opposite end of the thread 4 only passing through the central portion of the patch 3 to extend at the side thereof toward which the thread 4 is pulled.

Figure 19:
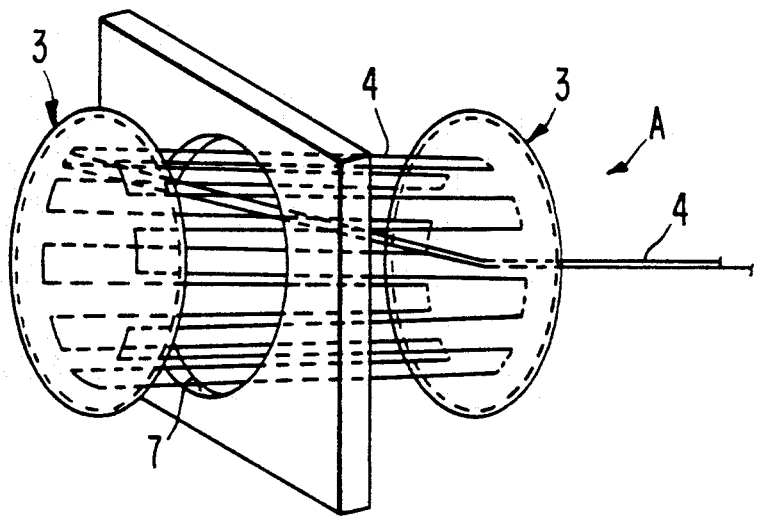
FIGS. 19, 20 and 21 are perspective views showing the process of implanting the occlusion device.
Figure 20:
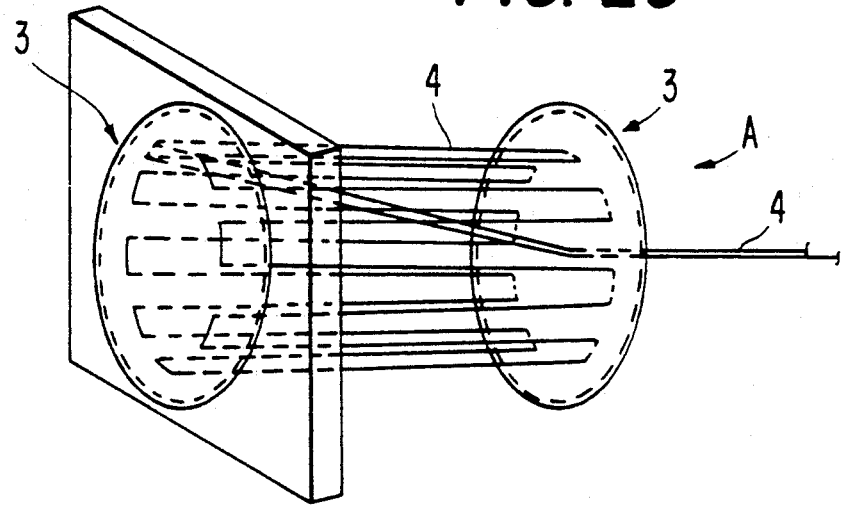
Figure 21:
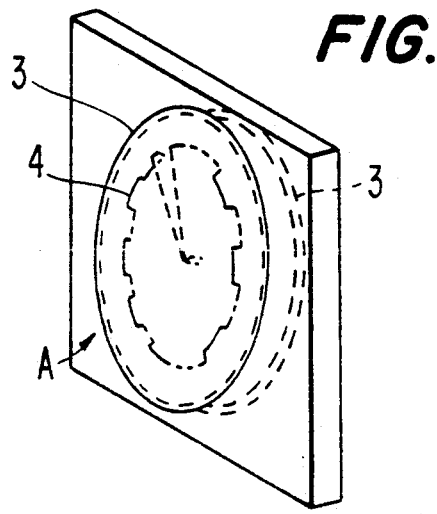

The occlusive device A shown in FIG. 18 is not carried by a carrying wire, but may be attached to a defect 7 by using a catheter 6 and a thread cutter 8 in a manner similar to that in the above-mentioned embodiment. FIGS. 19 through 21 perspectively show different steps of implanting the device A in a defect 7. The patches 3 of the occlusive device A may be pushed out of the catheter 6 by the outer metal tube 9 of the thread cutter 8.

Figure 24:
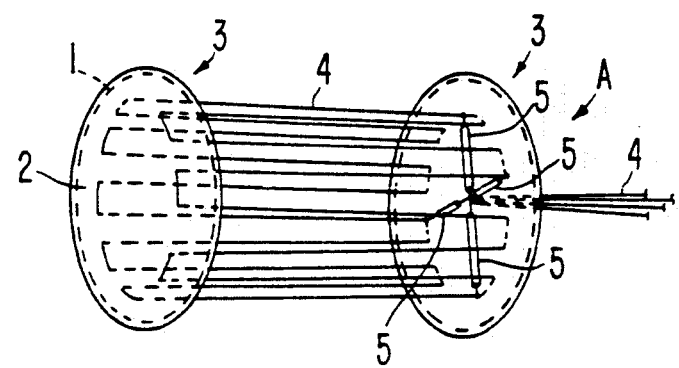
FIG. 24 is a perspective view of an occlusive device according to still another embodiment of the invention.

FIG. 24 shows a further embodiment of the invention. In the occlusive device A of this embodiment, four threads 4 extend from the periphery of the patch toward its center, where they are drawn outside, with each of the portions of the threads 4 which extend toward the center passing through a shrink-preventing tube 5.

Figure 25:
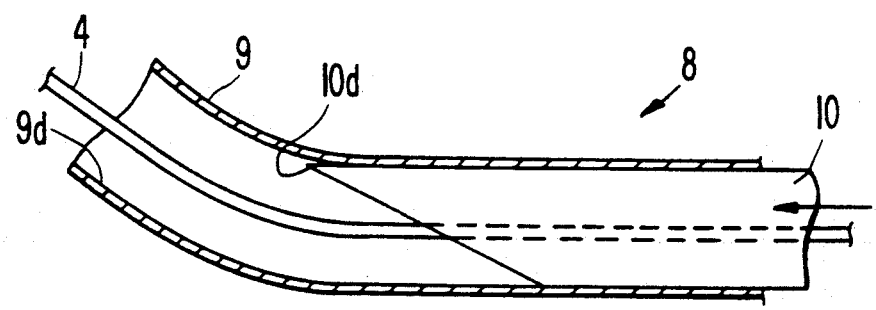
FIG. 25 is a sectional view showing a thread cutter according to another embodiment of the invention.
Figure 26:
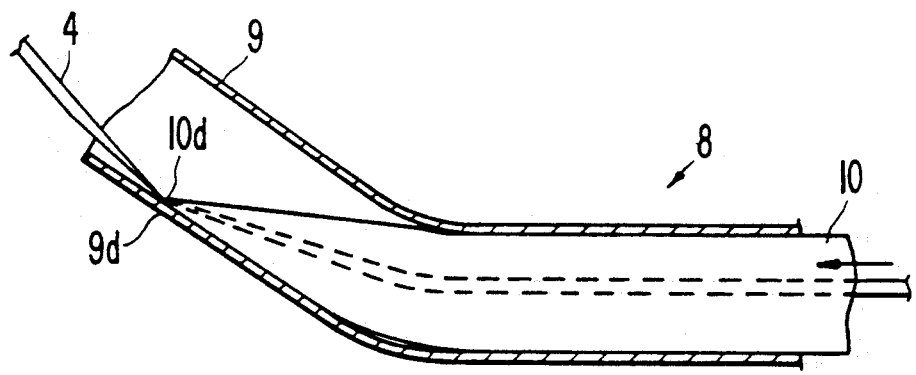
FIG. 26 is a view showing the operation of the thread cutter.

FIG. 25 shows another embodiment of the thread cutter. The thread cutter 8 comprises an outer metal tube 9 and an inner metal tube 10 disposed inside the tube 9. The outer metal tube 9 is bent at an obtuse angle at a portion 9d a little rearward of the front end of the tube so that the bent portion 9d is used for cutting. The front end portion of the inner metal tube 10 is cut aslant to form a cutter blade 10d. To cut the threads 4 by means of the thread cutter 8, the threads 4 are passed through the outer metal tube 9 and the inner metal tube 10. Then, the outer metal tube 9 is moved to bring the bent portion 9d near its front end to the portions of the threads 4 to be cut, and the inner metal tube 10 is advanced relative to the outer metal tube 9, so that the cutter blade 10d of the front end of the inner metal tube 10 is moved from the position shown in FIG. 25 to that shown in FIG. 26 so as to be pressed against the bent portion 9d of the outer metal tube 10, whereupon the above-mentioned threads 4 are strongly nipped between and cut by the cutter blade 10d of the front end of the inner metal tube 10 and the bent portion 9d of the outer metal tube 9.

Figure 27:
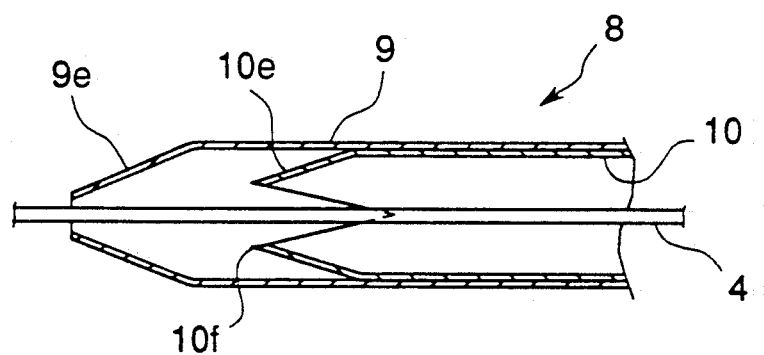
FIG. 27 is a sectional view of a thread cutter according to still another embodiment of the invention.
Figure 28:
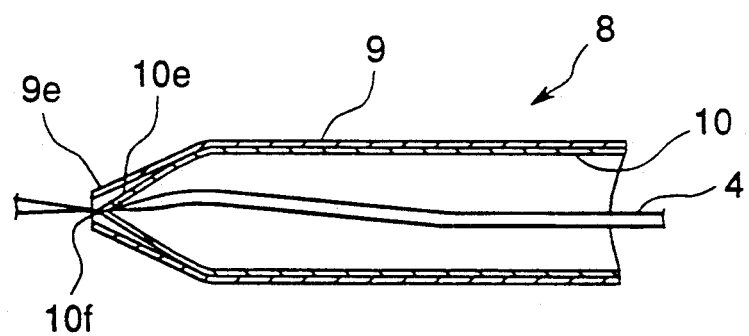
FIG. 28 is a view showing the operation of the thread cutter.

FIG. 27 shows still another embodiment of the thread cutter. In this thread cutter 8, the front end portion 9e of the outer metal tube 9 is tapered, and the front end portion 10e of the inner metal tube 10 is cut so as to form a two- or more than three-pronged fork, the edges of which are sharpened to form cutter blades 10f. With the threads 4 to be cut extending through the outer metal tube 9 and the inner metal tube 10, the two- or three-pronged front end portion 10e of the inner metal tube 10 is strongly pushed into the tapered front end portion 9e of the outer metal tube 9 as shown in FIG. 28, whereupon the cutter blades 10f formed by the edges of the two or three prongs are put together to nip and cut the threads. If the threads are not cut under the condition, by pulling them strongly it is possible to cut them.

The means for connecting the central portions of the patches put together at the opposite sides of a defect is not limited to the above-mentioned embodiments, but may be constructed as shown in FIGS. 29 through 37. These figures schematically show the constructions without the threads and the thread cutter.

Figure 29:
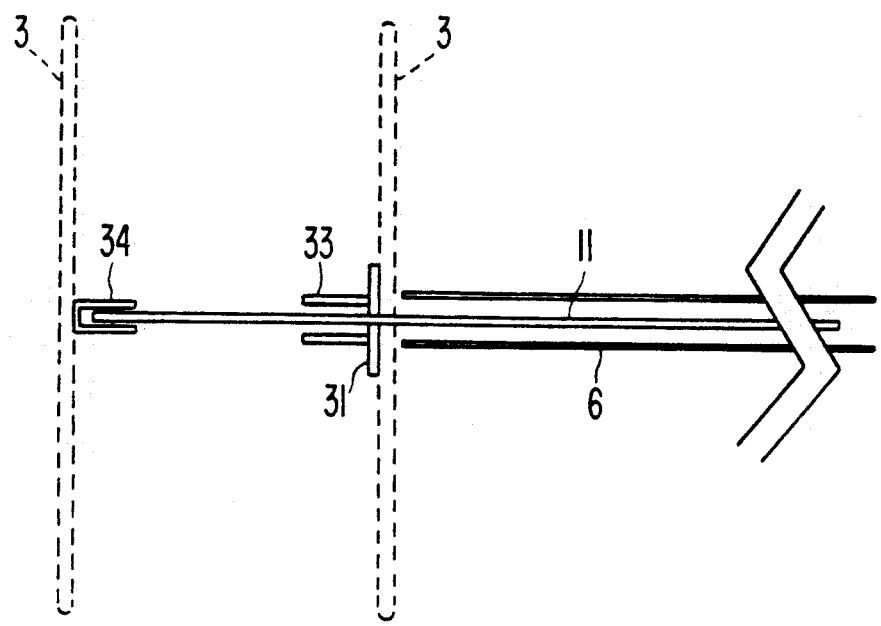
Figure 30:
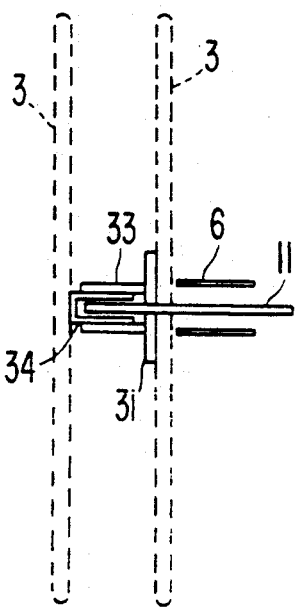
Figure 31:
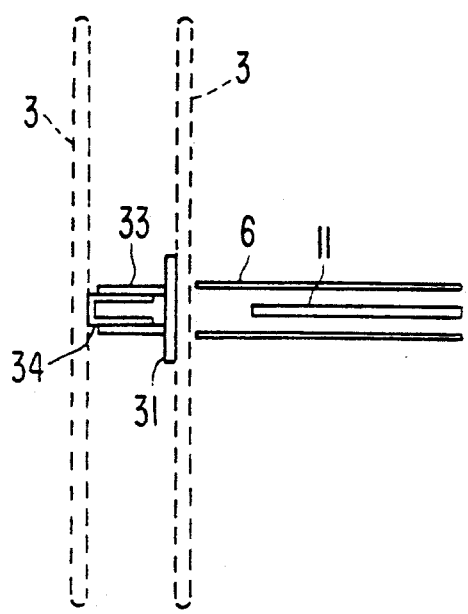

In the embodiment shown in FIGS. 29 through 31, the outer tube 33 and the inner tube 34 formed at the central portions of the patches 3 are merely tubular without an undercut on either of the outer and inner circumferential surfaces of the tubes. With the patches disposed as shown in FIG. 29, as the thread is pulled to put the patches together, the inner tube 34 is fitted into the outer tube 33 against the frictional resistance between the sliding surfaces of the tubes. Then, the carrying wire 11 is pulled strongly, whereupon the carrying wire 11 comes off the inner tube 34 so as to be separated from the patches 3.

Figure 32:
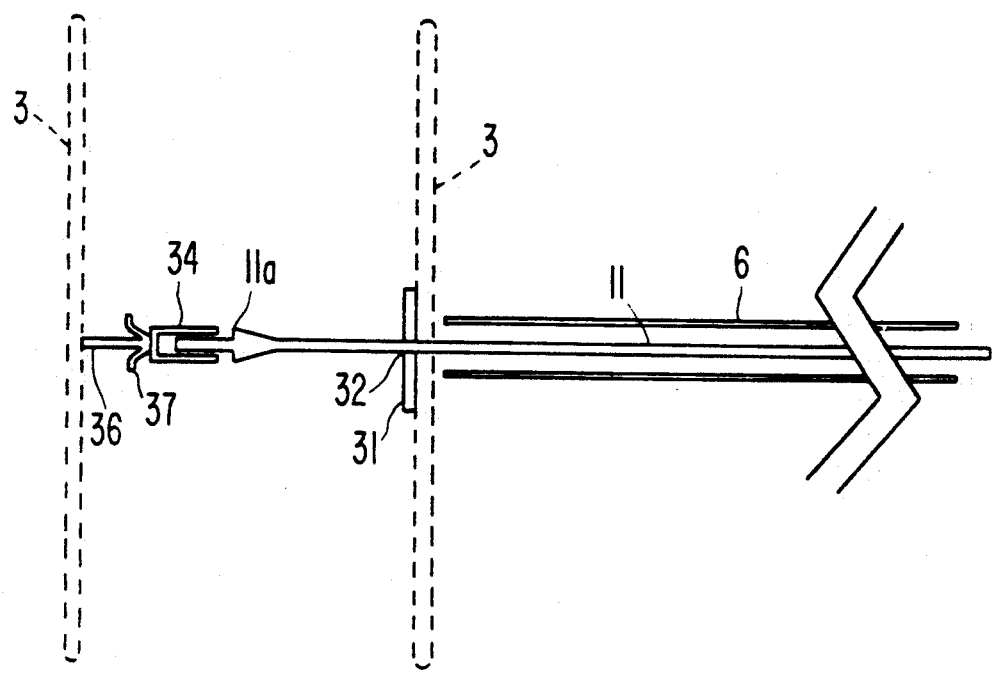
Figure 33:
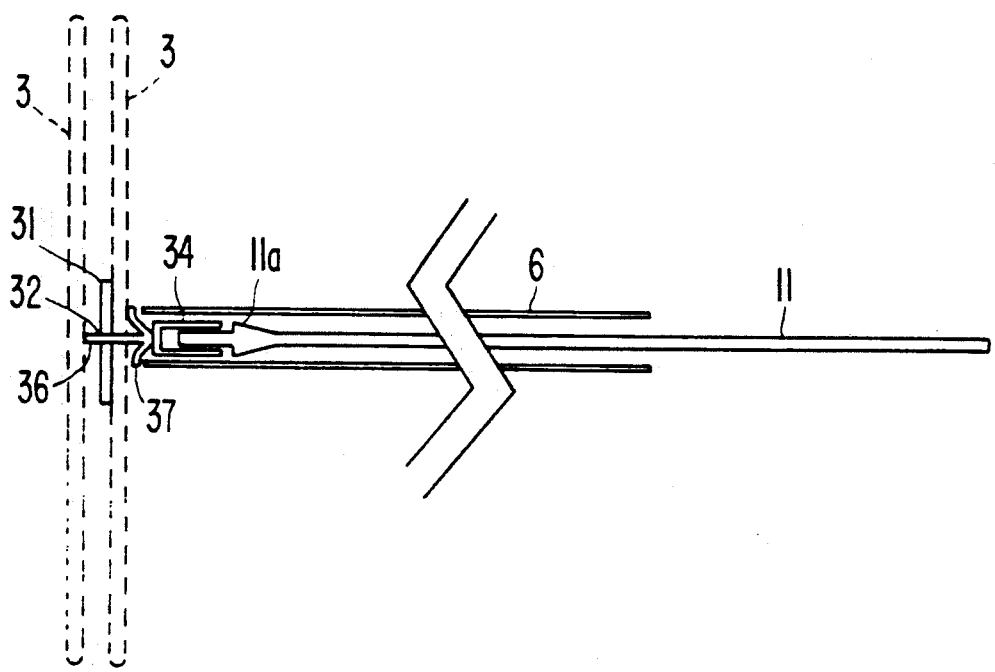
Figure 34:
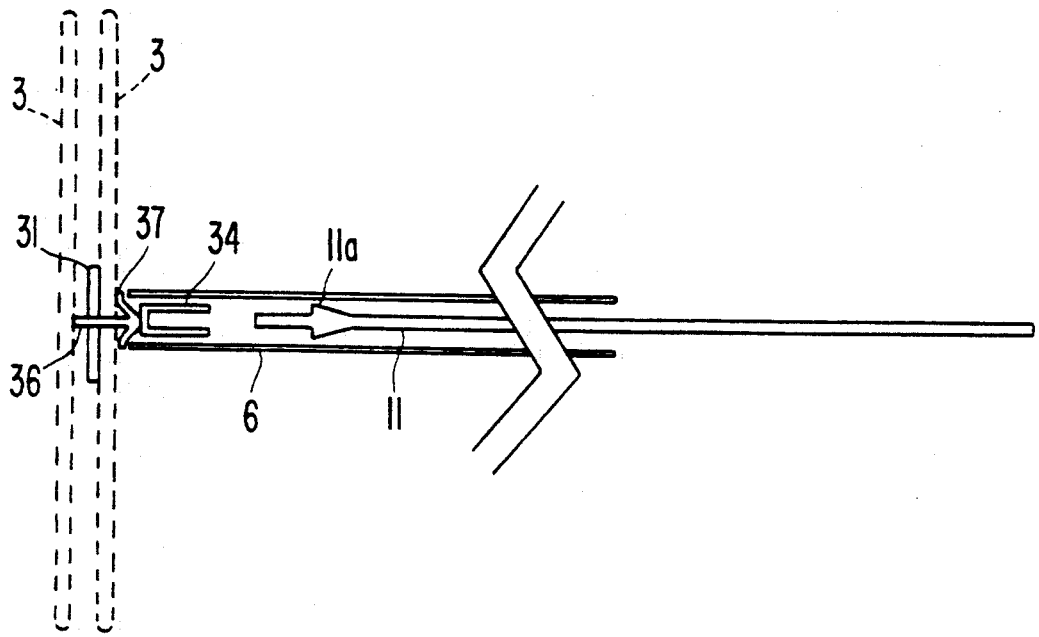
Figure 35:
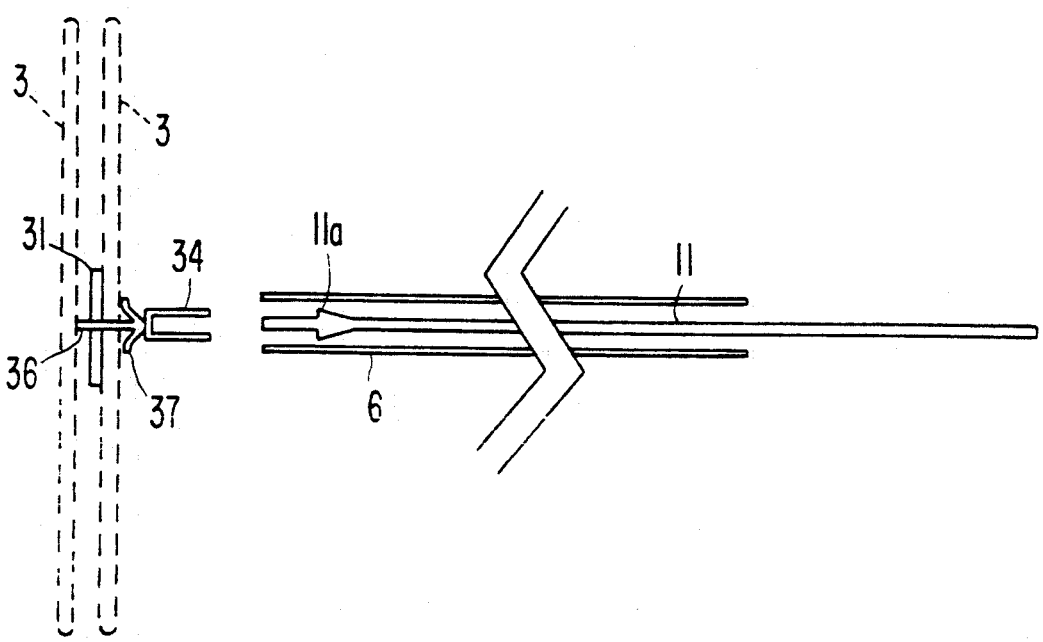
Figure 34:
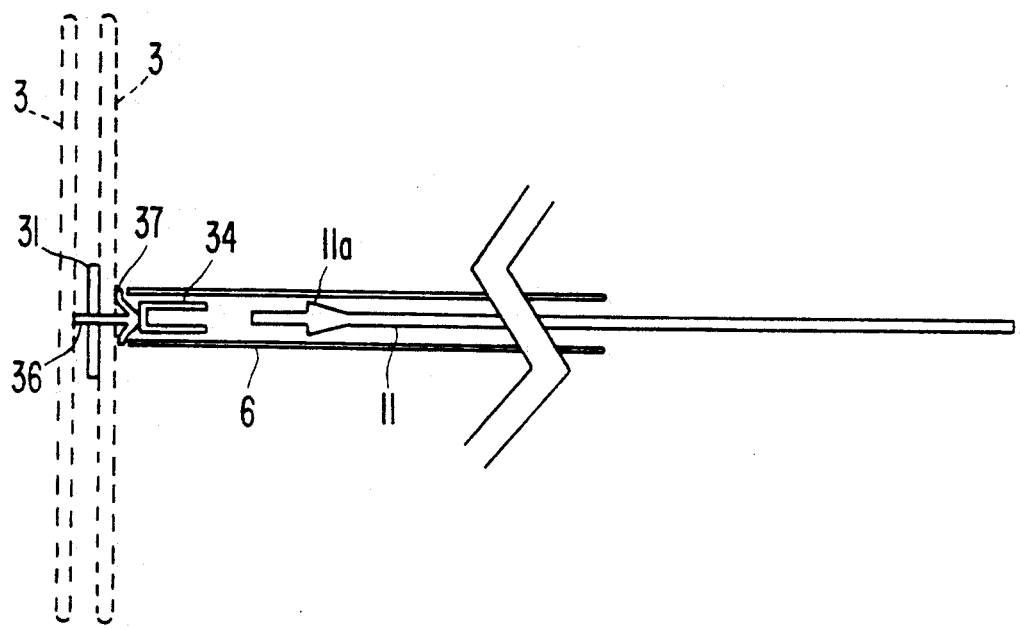
Figure 35:
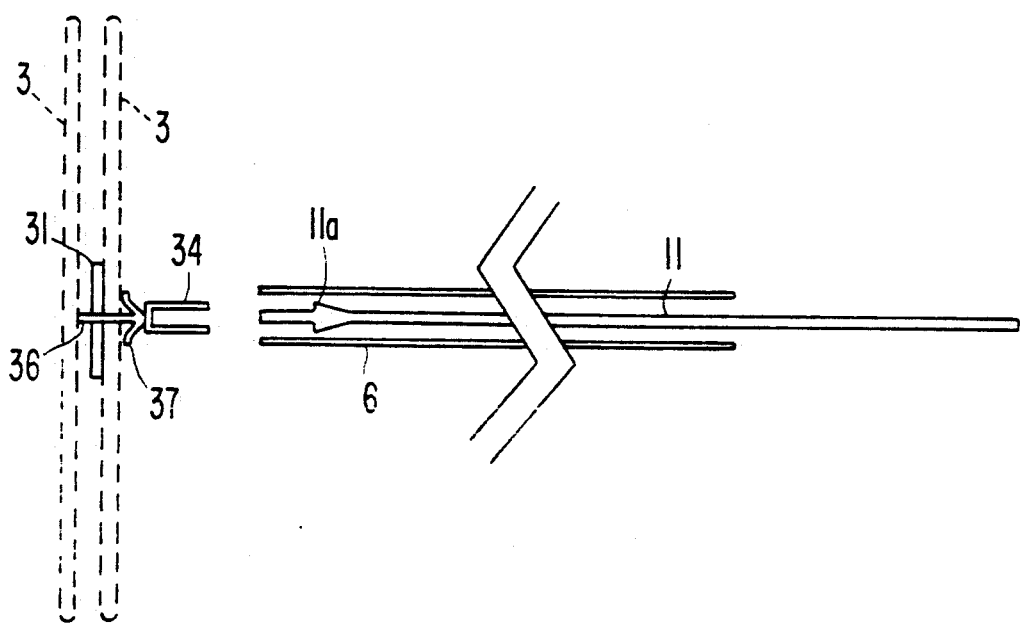

In the embodiment shown in FIGS. 32 through 35, a tube 34 corresponding to the above-mentioned inner tube is provided at the center of one of the patches 3 by means of a connecting wire 36 provided with an expanded, resiliently deformable fastening member 37 for preventing separation of the patches. A conical enlargement 11a is formed near the front end of the carrying wire 11 inserted into the above-mentioned tube 34. In this embodiment, with the patches 3 disposed as shown in FIG. 32, as the thread not shown is pulled to move the patches toward each other, the carrying wire 11 slides rearwardly through a reinforcing member 31 of rubber provided at the center of the rear patch. When the conical enlargement 11a on the carrying wire 11 has come near the rear patch 3, the catheter 6 is fixed with its front end abutting on the rear patch 3, and the carrying wire 11 is pulled, so that the conical enlargement 11 together with the previously mentioned tube 34 and separation-preventing fastening member 37 passes through the central hole 32 of the reinforcing member 31 while resiliently expanding it as shown in FIG. 33. With the front end of the catheter 6 held against the rear patch 3, the carrying wire 11 is strongly pulled back, whereupon the wire 11 comes off the tube 34 as shown in FIG. 34. Then the catheter 6 and the carrying wire 11 are drawn out as shown in FIG. 35.

In the embodiment shown in FIG. 36, the separation-preventing fastening member 37 is omitted.

In the embodiment shown in FIG. 37, instead of the separation-preventing fastening member 37, the tube 34 is formed at its base with an integral expanded fastening member 34a.

POSSIBLE APPLICATIONS IN INDUSTRY

The device for nonoperatively occluding a defect is useful for nonoperative treatment of arterial septal defect, ventricular septal defect, patent ductus arteriosus, dissecting aneurysm, ruptured aneurysm, etc.

I claim:

1. A device for nonoperatively occluding a defect characterized by a pair of patches, each comprising a flexible, foldable annular frame and a piece of cloth stretched over and fixed to the frame are arranged so as to face each other and sewed together by a thread in such a manner that as the thread led out of one of the patches is drawn, the patches are moved to approach each other.

2. The device for nonoperatively occluding a defect described in claim 1 and characterized by the two patches being sewed with the thread along a coaxial circle a little inward of the circumferential edge of each of the patches.

3. The device for nonoperatively occluding a defect described in claim 1 and characterized by the end portion of the thread for sewing the patches together being led out of the central portion of one of the patches.

4. The device for nonoperatively occluding a defect described in claim 1 and characterized by shrink-preventing members provided on that surface of one of the patches which faces the surface of the other of the patches so as to extend from a position a little inward of the outer circumferential edge of the one patch to a position near the center thereof.

* * * * *